(12) United States Patent
DeMello (10) Patent No.: US 6,544,197 B2
(45) Date of Patent: Apr. 8, 2003

(54) COMPOSITE GUIDEWIRE

(75) Inventor: Richard M. DeMello, Acton, MA (US)

(73) Assignee: Radius Medical Technologies, Inc., Maynard, MA (US)

( * ) Notice: Subject to any disclaimer, the term of this patent is extended or adjusted under 35 U.S.C. 154(b) by 0 days.

(21) Appl. No.: 09/778,566

(22) Filed: Feb. 7, 2001

(65) Prior Publication Data

US 2002/0049392 A1 Apr. 25, 2002

Related U.S. Application Data

(63) Continuation-in-part of application No. 09/693,547, filed on Oct. 20, 2000.

(51) Int. Cl.[7] .......................... A61B 5/00; A61M 25/00
(52) U.S. Cl. ............................................... 600/585
(58) Field of Search ................................. 600/585, 434, 600/486, 561; 604/170.01, 531, 95.01, 164.13, 528, 533, 538

(56) References Cited

U.S. PATENT DOCUMENTS

| 4,873,983 A | | 10/1989 | Winters | |
| 4,953,553 A | * | 9/1990 | Tremulis | 600/434 |
| 4,984,581 A | * | 1/1991 | Stice | 600/434 |
| 5,067,489 A | | 11/1991 | Lind | |
| 5,769,796 A | | 6/1998 | Palermo et al. | |
| 6,193,706 B1 | * | 2/2001 | Thorud et al. | 604/103.04 |

FOREIGN PATENT DOCUMENTS

| EP | 0806220 | 11/1997 |
| EP | 0838230 | 4/1998 |
| EP | 0868924 | 10/1998 |
| EP | 0982046 | 3/2000 |

* cited by examiner

Primary Examiner—Max F. Hindenburg
Assistant Examiner—Brian Szmal
(74) Attorney, Agent, or Firm—Cesari and McKenna, LLP (57) ABSTRACT

A composite guidewire includes a solid central core of super elastic material and one or more core overlays of non-super elastic material. A coupling tube fits over the proximal end of the core, and a coil, which may be radiopaque, fits over the distal end of the core and attaches to a distal end of the coupling tube. A flat safety wire that is positioned between the distal portion of the coupling tube and the core also attaches to the distal end of the tube. The safety wire extends the length of the coil and attaches to both the distal and the proximal ends of the coil. The guidewire's proximal end may be a non-super elastic core extension shaped at its distal end to overlap and mechanically inter-lock with a proximal end of the core and the coil and safety wire may extend beyond the distal end of the core.

29 Claims, 6 Drawing Sheets

COMPOSITE GUIDEWIRE

CROSS-REFERENCE TO RELATED APPLICATIONS

The present application is a continuation-in-part of commonly assigned copending U.S. patent application Ser. No. 09/693,547 which was filed on Oct. 20, 2000, by Richard M. DeMello for a COMPOSITE GUIDEWIRE and is hereby incorporated by reference.

BACKGROUND OF THE INVENTION

1. Field of the Invention

The invention relates generally to guidewires for directing catheters or other medical instruments through the cardiovascular system.

2. Background Information

Guidewires for use in, for example, percutaneous transluminal coronary artery angioplasty (PTCA), must be thin and flexible enough to advance through small arteries within the coronary vasculature. These wires must also be sturdy enough to be manipulated from the outside of the body, such that a distal end of the wire can be brought into contact with a selected region of the coronary artery. Further, they must be strong enough to survive a "pull test" without breaking, to ensure that they do not come apart in the body.

Numerous guidewire designs exist. These designs have typically been made from stainless steel materials and may have platinum coils added to increase radiopacity. Coatings such as PTFE, silicon, and hydrophilic materials may be added to reduce friction and improve movement of devices that are passed over the guidewire.

Stainless steel guidewires are inherently stiff and offer excellent support along the proximal shaft portion of the guidewire. The distal ends of these wires may also be deliberately bent or shaped to aid in steering the guidewire into a particular vessel or lumen. The material, however, is susceptible to further plastic deformation during use and has been known to permanently deform and kink. The deformation is particularly noticeable when the guidewire is manipulated through a tortuous anatomy.

More recently, guidewires have been made from "super elastic" materials such as Nitinol, with coils added for radiopacity and coatings for lubricity, as mentioned above. The super elastic guidewires offer excellent kink resistance, and provide exceptional torque control when placed within tortuous anatomies. The super elastic material, however, is significantly less stiff than stainless steel and therefore does not provide a high level of support along the proximal portion of the guidewire. Further, the super elastic material cannot be easily shaped or reshaped at the distal tip to aid in steering the guidewire.

Composite construction guidewires combine a proximal portion of stainless steel with a distal portion of super elastic material, to take advantage of the best performance characteristics of both materials. Unfortunately, it is very difficult to attach non-super elastic materials to super elastic materials. The joint cannot, for example, be held together by braising or welding. Accordingly, a special coupling must be used to lock the materials together.

In a known prior system the ends of the two guidewire portions, that is, the ends of the two materials, are butted against one another and a sleeve, which made of non-super elastic material, is fit over the joint. The guidewire portions are then held together by crimping, spot welding or gluing the sleeve in place. The coupling relies mainly on the mechanical interface between the two portions of the guidewire. If a mismatch in the cross-sectional dimensions exists, the distal and proximal portions may separate. Further, the repeated torqueing and bending that occurs when the guidewire is manipulated through the cardiovascular system may fatigue the coupling and result in the separation of the distal and proximal portions of the guidewire within the patient's body.

SUMMARY OF THE INVENTION

A composite guidewire constructed in accordance with the invention includes a solid central core that is made out of super elastic material. A coupling tube which is usually of a non-super elastic material fits over the proximal end of the central core, and a coil, which may be radiopaque, fits over the distal end of the super elastic central core and attaches to a distal end of the coupling tube. A flat safety wire or ribbon of a non-super elastic material that is positioned between the distal portion of the coupling tube and the central core also attaches to the distal end of the coupling tube. The safety wire extends the length of the coil and attaches to both the distal and the proximal ends of the coil. The coil, the coupling tube and the safety wire attach to one another by soldering, brazing, welding or adhesives, which ensures that the joints are strong and the various components of the guidewire do not pull apart. The tube may also be crimped at various locations along its length, to prevent rotational and axial movement between the non-super elastic tube and the super elastic core. An atraumatic tip fits over the end of the guidewire and attaches to the coil and the safety wire by brazing welding or adhesive, to provide a cushioned end.

The coil and the safety wire may extend beyond the distal end of the central core, such that the distal end of the guidewire can be readily shaped for steering.

The guidewire may also be formed with a composite core that includes the super elastic core and a non-super elastic core extension, which is shaped at its distal end to overlap and mechanically inter-lock with a proximal end of the super elastic core. The coupling tube then extends partially over a portion of the non-super elastic core extension and partially over a portion of the super elastic core, with the proximal end of the coupling tube attaching to the core extension by brazing, welding or adhesives. The coil that fits over the distal end of the super elastic core mates at its proximal end with the distal end of the coupling tube. The safety wire runs from the end of the core extension to distal end of the guidewire, and attaches to the core extension, the coupling tube, the coil and the tip.

In another variation of the guidewire, instead of interlocking the opposing ends of the super elastic core and the non-super elastic core extension, those ends may be butted and the core and core extension provided with longitudinal flats so that the safety wire can extend lengthwise between those elements and the coupling tube. Then the remaining radial space between the core-core extension and the coupling tube is filled with epoxy resin. The epoxy coupled with the irregular cross-sections of the core-to-core extension assembly creates a strong joint able to transmit considerable torque without failure.

The various components of the composite guidewire embodiments attach to components of like or similar materials, such that the joints between the components can be formed by brazing, welding or adhesives. The joints are thus strong, and do not fatigue as readily as joints between the dissimilar non-super elastic and super elastic materials that occur in known prior composite guide wires. The guidewire, with its super elastic core, takes advantage of the associated resistance to kinking and torque control. Further, the coupling tube overlaid on the super elastic core provides both support for the proximal portion of the guidewire and the ability to shape the distal end of the guidewire.

BRIEF DESCRIPTION OF THE DRAWINGS

The invention description below refers to the accompanying drawings, of which.

DETAILED DESCRIPTION OF AN ILLUSTRATIVE EMBODIMENT

Figure 1:
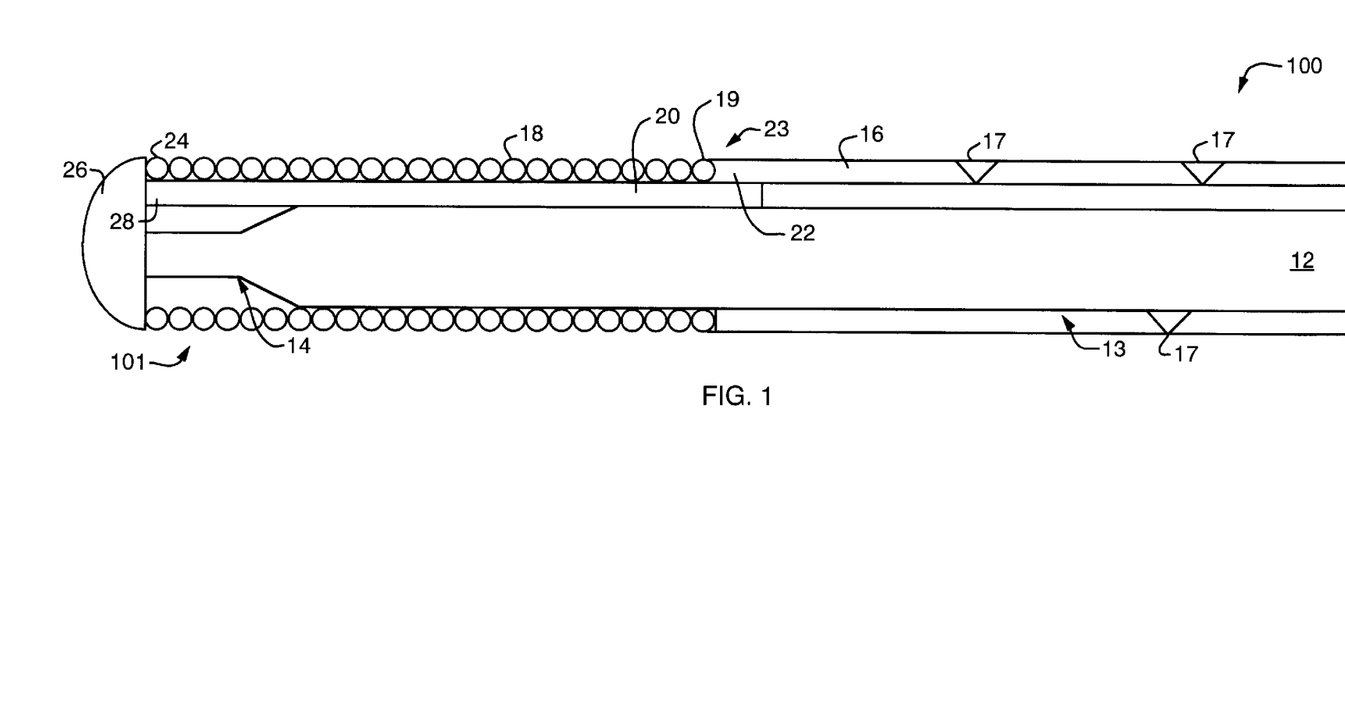
FIG. 1 is a cross-sectional view of a guidewire constructed in accordance with the invention.

Referring now to FIG. 1, a composite guidewire 100 includes a central core 12 that is made of super elastic material such as, for example, Nitinol. A coupling tube 16 of a non-super elastic material fits over a proximal portion 13 of the core 12 and attaches at a distal end 22 to a proximal end 19 of a coil 18 that fits over the distal end 14 of the core 12. A flat ribbon-like safety wire 20, which is positioned between a distal portion 23 of the coupling tube 16 and the core 12 and extends to the distal end 101 of the guidewire, attaches to both the coupling tube 16 and the coil 18. The coupling tube 16, coil 18 and the safety wire 20 are all of non-super elastic materials, e.g. stainless steel, and can be attached to one another by adhesives, brazing or welding. The tube 16 may also be attached to the super elastic core 12 by crimping at various locations 17, to prevent relative rotational or axial movement.

An atraumatic tip 26 that attaches to the distal ends 24 and 28 of the coil 18 and the safety wire 20 may be included, to cushion the distal end 101 of the guidewire 100. The distal end 14 of the core 12 may be tapered for added flexibility at the distal end 101 of the guidewire. Further, the windings 19 of the coil 18 may be slightly spread apart to provide even greater flexibility.

Figure 2:
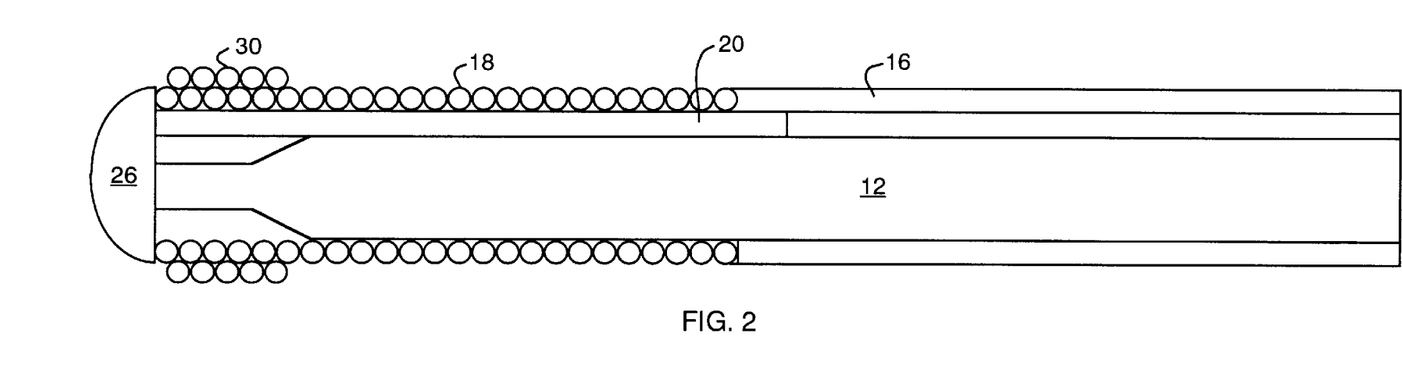
FIG. 2 depicts the guidewire of FIG. 1 with an additional radiopaque coil.

The coil 18 may be radiopaque and thus visible to x-rays. Alternatively, the coil 18 may be non-radiopaque and a second shorter coil 30 may be fit over the coil 18 to provide the visibility, as shown in FIG. 2. As desired, the coil 18 may be tapered such that the guidewire has a uniform diameter over its length.

Figure 3:
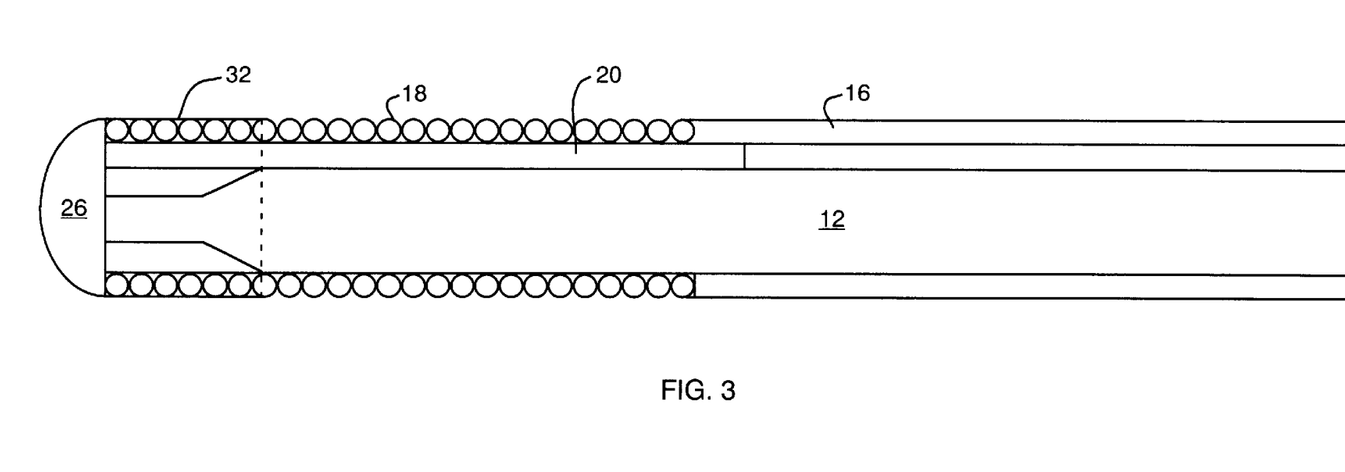
FIG. 3 depicts the guidewire of FIG. 1 with a radiopaque cover.

The radiopacity may instead be provided by a radiopaque plastic cover 32 (FIG. 3) that fits over the distal end of the wire and is attached to the coil 18 by, for example, heat shrinking. The cover 32 may fit over the tip 26 or may incorporate a cushion and thus replace the tip.

Figure 4:
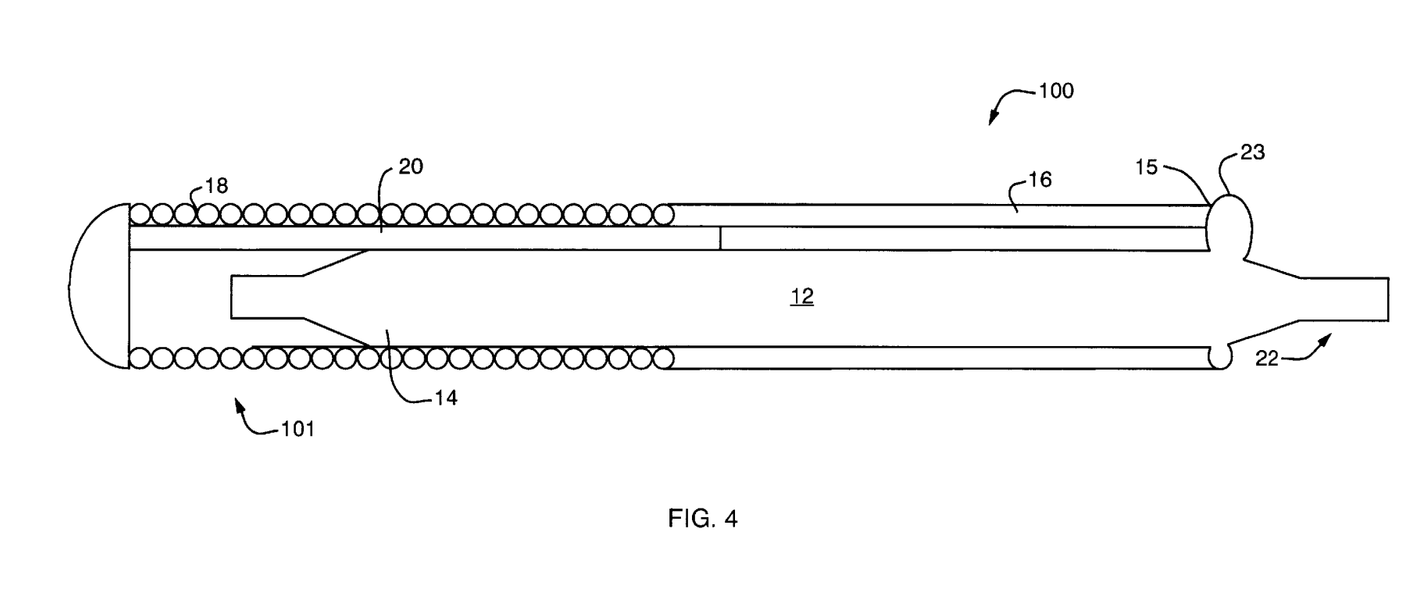
FIG. 4 is a cross-sectional view of an alternative guidewire.

Referring now to FIG. 4, the flexibility of the distal end 101 of the guidewire 100 may be further increased by extending the coil 18 and safety wire 20 beyond the distal end 14 of the super elastic core 12. The distal end 101 of the guidewire 100 can thus be readily shaped or bent, to aid in the steering of the guidewire through the body. As also depicted in the drawing, the proximal end 22 of the central core 12 may be extended beyond the proximal end 15 of the coupling tube 16, such that removable guidewire extensions (not shown) can be fit over the end of the core. In addition, the proximal end 22 of the core 12 may be shaped as a stop 23 that further secures the coupling tube 16 against axial movement relative to the core. As discussed, the coupling tube may be crimped to the core in various locations 17 (FIG. 1), to prevent both axial and rotational movement relative to the core.

Figure 5:
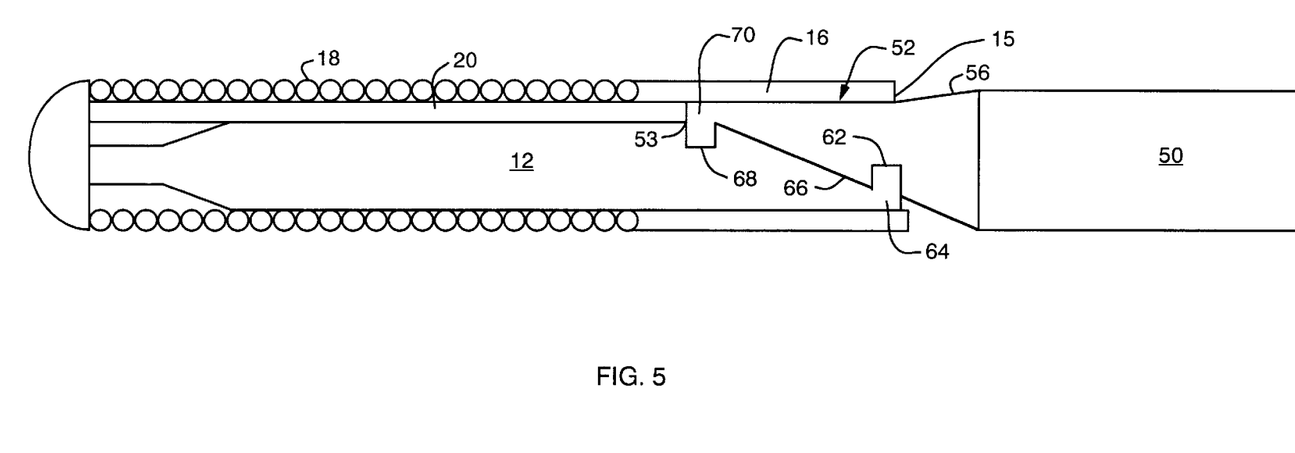
FIG. 5 is a similar view of another alternative guidewire.

Referring now to FIG. 5, the guidewire may have a composite core 60 that includes the super elastic core 12 and a core extension 50 of a non-super elastic material, e.g. stainless steel, that fixedly attaches to the super elastic core 12. The extension 50 is shaped at its distal end 52 to mate with a shaped proximal end 54 of the super elastic core 12, such that the core and core extension inter-lock.

As depicted in the drawing, the outer surface 56 of the distal end 52 of the core extension 50 tapers slightly, to meet the proximal end 15 of the coupling tube 16. Surface 56 tapers to approximately one-half the diameter of the core extension and includes a recess 62 for receiving a tab 64 that extends from an inner surface 66 of the super elastic core 12. The inner surface 66 of the core 12 tapers to approximately one-half the diameter of the core and includes a recess 68 for receiving a tab 70 that extends from the core extension 50. The tapered ends of the core 12 and the extension 50 thus overlap and inter-lock to produce a composite core 60 of essentially uniform diameter with a mechanically tight joint.

The coupling tube 16 extends from the proximal end of the core 12 to meet the proximal end of the coil 18. The coupling tube thus also extends over and attaches to the tapered outer surface 56 of the distal portion 52 of the core extension 50. The safety wire 20 attaches to and extends from a distal end wall 53 of the non-super elastic core extension 50 to the distal end 24 of the coil 18. As discussed above, the safety wire 201, the coil 18 and the core extension 50 all being of non-super elastic compatible materials may be attached to one another by brazing, welding or adhesives.

The coupling tube 20 which overlaps both the core 12 and the extension 50 may be made of super elastic material or non-super elastic material. The coupling tube then attaches to the similar material coil or coil extension by brazing, welding, or adhesives. The selection of material for the coupling tube depends on the desired flexibility of the joint portion of the tube.

Figure 6:
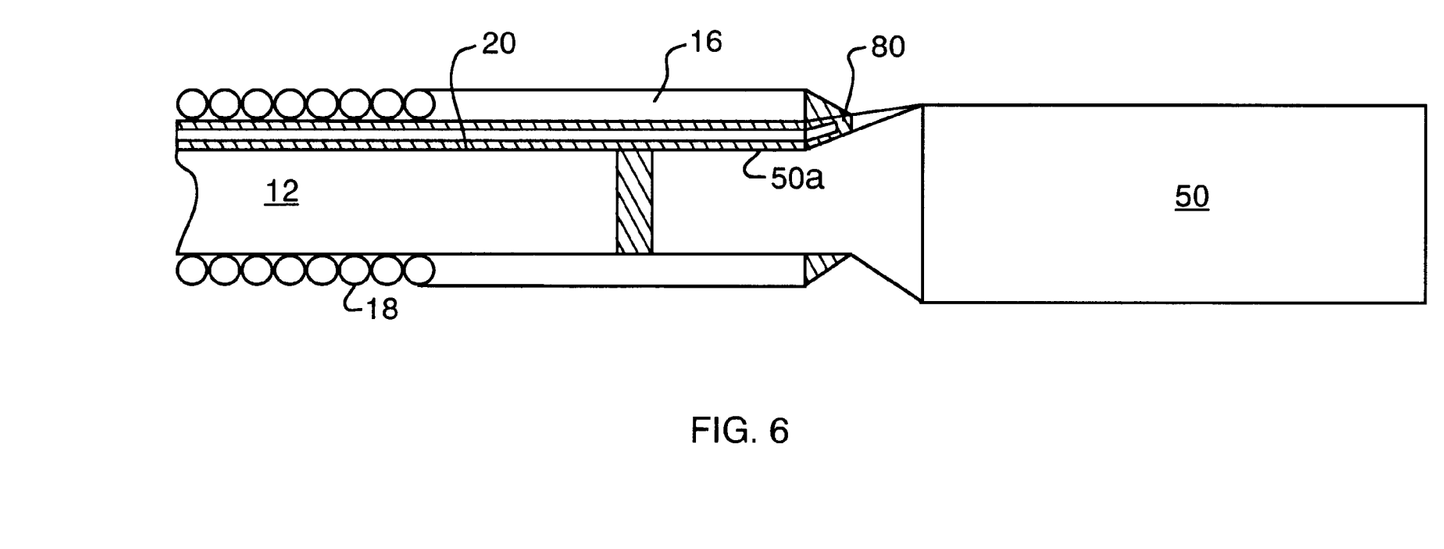
FIG. 6 is a similar view of yet another guidewire embodiment.

Refer now to FIG. 6, which shows a guidewire with a somewhat different connection between the super elastic core 12 and the non-super elastic core extension 50. Instead of interlocking the opposing ends of those members, they are provided with squared off ends which are butted more or less midway along within the coupling tube 16.

Also, the core and core extension are provided with longitudinal flats 12a and 50a, respectively, to provide clearance for the safety wire 20. Wire 20 extends from a point just beyond the proximal end of coupling tube 16 to the distal end of coil 18. Then, the entire remaining space within coupling tube 16 is filled with epoxy resin 80 as shown by the stippling in FIG. 6. Since the core 12 and core extension 50, with their flats, have irregular shapes, the epoxy creates a strong joint between the core and core extension that is able to transmit substantial torque without failure.

As before, the non-super elastic components of the guidewire, i.e., coil 18, safety wire 20 and tube extension 50 may be connected by welding, brazing, adhesives or the like.

Further, the coupling tube 16, which may be made from either super elastic material or non-super elastic material, attaches to the core or the core extension, as appropriate, by welding, brazing, adhesives or the like.

In summary, the composite guidewire includes a super elastic core and various non-super elastic components. The non-super elastic components, which overlay the super elastic core, attach to one another by brazing, welding or adhesives and thus form strong joints between a distal coil, a ribbon wire and a proximal end of the guidewire, and as appropriate, a non-super elastic coupling tube that extends over the proximal end of the super elastic core. The coupling tube and/or the non-super elastic core extension provides support for the proximal end of the guidewire, while the safety wire and coil provide a flexible and shapeable distal end. Accordingly, the guidewire combines the best qualities of non-super elastic and super elastic materials without sacrificing joint strength.

The foregoing description has been limited to a specific embodiment of this invention. It will be apparent, however, that variations and modifications may be made to the invention, including substituting other super elastic and/or non-super elastic materials for those specifically named herein, with the attainment of some or all of its advantages. Therefore, it is the object of the appended claims to cover all such variations and modifications as come within the true spirit and scope of the invention.

What is claimed is:

1. A composite guidewire including:
   a core of super elastic material, the core having a distal portion and a proximal portion;
   a coupling tube extending over the proximal portion of the core, the tube having a distal end and a proximal end, the coupling tube being adapted to engage the core at various locations so as to prevent rotational and axial movement of the coupling tube with respect to the core;
   a safety wire of a non-super elastic material overlying the core, the safety wire having a distal end that extends to the distal end of the core and a proximal end that extends beyond the distal end of the coupling tube to an attachment location adjacent to a distal end of the coupling tube;
   a coil engaged over the distal portion of the core, the coil having a distal end that attaches to the safety wire and a proximal end that engages a distal end of the coupling tube, the coil overlying the safety wire; and
   a tip attached to the distal end of said coil and the distal end of said safety wire.

2. The composite guidewire of claim 1 further including
   a core extension of non-super elastic material, the core extension having a distal end that is adjacent a proximal end of the core, and
   the safety wire attaches at a proximal end to a distal portion of the core extension.

3. The composite guidewire of claim 2 wherein the core and the core extension include longitudinal flats for receiving the safety wire.

4. The composite guidewire of claim 3 wherein the space between the coupling tube and the core and core extension is filled with epoxy resin.

5. The composite guidewire of claim 4 wherein the coupling tube is made of super elastic material.

6. The composite guidewire of claim 4 wherein a distal end segment of the core is tapered.

7. The composite guidewire of claim 4 wherein the coil and safety wire extend beyond the distal portion of the core.

8. The composite guidewire of claim 4 wherein the coil is radiopaque.

9. The composite guidewire of claim 4 wherein
   the coil is non-radiopaque, and
   the guidewire further includes a radiopaque coil engaged over the non-radiopaque coil.

10. The composite guidewire of claim 4 wherein
    the coil is non-radiopaque, and
    the guidewire further includes a radiopaque cover engaged over the tip and the distal end of the coil.

11. The composite guidewire of claim 1 wherein a distal end segment of the core is tapered.

12. The composite guidewire of claim 1 wherein the proximal end of the core extends beyond the proximal end of the coupling tube and is shaped as a stop for the coupling tube.

13. The composite guidewire of claim 1 further including
    a core extension of a non-super elastic material, the core extension having a distal end portion fixedly mated with said proximal end portion of the core, and
    wherein the proximal end portion of the core is fixedly mated with the distal end portion of the core extension.

14. The composite guidewire of claim 13 wherein the distal end portion of the extension and the proximal end portion of the core have interfitting parts.

15. The composite guidewire of claim 4 wherein
    the proximal end portion of the core includes a tab, and
    the distal end portion of the extension includes a recess for receiving the tab, or vice versa.

16. The composite guidewire of claim 1 further comprising a radiopaque cushioning cover attached to the distal end of the coil.

17. The composite guidewire of claim 16 wherein a distal end of the core is tapered.

18. The composite guidewire of claim 16 wherein the coil and the wire extend beyond a distal end of the core.

19. The composite guidewire of claim 16 wherein the cushioning cover includes a plastic cushioning tip.

20. A composite guidewire including:
    a core that includes a first section of super elastic material and a second section of a non-super elastic material;
    a super elastic tube section extending over a distal segment of the second section and a proximal segment of the first section, the tube being attached to a proximal section of the first section of the core and the tube being adapted to engage the core at various locations so as to prevent rotational and axial movement of the tube section with respect to the core;
    a wire of a non-super elastic material overlying the core and being attached to the distal end of the second section of the core and extending to a distal end of the first section of the core the wire extending beyond a distal end of the tube section;
    a coil engaged over the distal segment of the first core section, the coil having a distal end attached to a distal end of the wire and a proximal end that engages a distal end of the tube section, the coil overlying the wire; and
    a tip attached to the distal end of the coil and the distal end of the wire.

21. The composite guidewire of claim 20 further comprising a core extension, and wherein the core and the core extension each include longitudinal flats for receiving the safety wire.

22. The composite guidewire of claim 20 wherein
    the first section of the core is shaped at a proximal end to mate with the distal end of the second section of the core, and the distal end of the second section of the core is shaped to mate with the proximal end of the first section of the core.

23. The composite guidewire of claim 22 wherein the distal end of the second section of the core tapers to approximately one-half of the diameter of the core and includes a protruding tab, and the proximal end of the first section of the core tapers to approximately one-half of the diameter of the core and includes a recess for receiving the tab.

24. The composite guidewire of claim 23 wherein the proximal end of the first section of the core includes a second tab, and the distal end of the second section of the core includes a second recess for receiving the second tab.

25. A composite guidewire including:

a core that includes a first section of super elastic material and a second section of a non-super elastic material;

a super elastic tube section extending over a distal segment of the second section and a proximal segment of the first section, the tube being attached to a proximal section of the first section of the core and the tube being adapted to engage the core at various locations so as to prevent rotational and axial movement of the tube section with respect to the core;

a wire of a non-super elastic material overlying the core and being attached to the distal end of the second section of the core and extending to a distal end of the first section of the core the wire extending beyond a distal end of the tube section;

a coil engaged over the distal segment of the first core section, the coil having a distal end attached to a distal end of the wire and a proximal end that engages a distal end of the tube section, the coil overlying the wire; and a tip attached to the distal end of the coil and the distal end of the wire.

26. The composite guidewire of claim 25 wherein the space between the coupling tube and the core extension if filled with epoxy resin.

27. The composite guidewire of claim 26 wherein the coil is radiopaque.

28. The composite guidewire of claim 26 wherein the coil is non-radiopaque, and the guidewire further includes a radiopaque coil engaged over the non-radiopaque coil.

29. The composite guidewire of claim 26 wherein the coil is non-radiopaque, and the guidewire further includes a radiopaque plastic cover engaged over the tip and the distal end of the coil.

* * * * *